United States Patent [19]

Stahl

[11] 4,310,401
[45] Jan. 12, 1982

[54] ELECTROCHEMICAL SENSOR CONSTRUCTION ESPECIALLY AUTOMOTIVE-TYPE EXHAUST GAS ANALYZING SENSOR

[75] Inventor: Roland Stahl, Freiberg, Fed. Rep. of Germany

[73] Assignee: Robert Bosch GmbH, Stuttgart, Fed. Rep. of Germany

[21] Appl. No.: 181,841

[22] Filed: Aug. 27, 1980

[30] Foreign Application Priority Data

Sep. 13, 1979 [DE] Fed. Rep. of Germany ....... 2937048

[51] Int. Cl.³ ............................................. G01N 27/58
[52] U.S. Cl. ................................................. 204/195 S
[58] Field of Search ............................ 204/195 S, 1 S

[56] References Cited
U.S. PATENT DOCUMENTS 4,157,282  6/1979  Riddel ................................ 204/1 T
4,193,965  3/1980  Cullingford et al. ....... 204/195 S X Primary Examiner—G. L. Kaplan
Attorney, Agent, or Firm—Frishauf, Holtz, Goodman & Woodward

[57] ABSTRACT

To permit ease of manufacture and eliminate the necessity to apply a heater to the inside of a closed tube, a solid electrolyte, in elongated plate form is located within a housing which includes a sealing element separating the elongated plate into two portions; one portion (11/1) is exposed to the gas to be tested, the other portion (11/2) separated from the first portion (11/1) by a gas tight seal (16) positioned in the housing (12) is exposed to a reference gas, typically the oxygen in ambient air; the elongated plate extends to a terminal end portion (11/3) retained in a ceramic holder (14) for example by means of a plastic bushing (33), formed with an opening (34) to permmit access of the reference portion (11/2) to ambient air. Preferably, the electrodes (37, 38) are applied to one major surface (36) of the plate, the opposite side (40) having one or more heater elements (42, 44) applied thereto, for example by printing or vapor deposition and in alignment with the respective electrodes.

8 Claims, 4 Drawing Figures

ELECTROCHEMICAL SENSOR CONSTRUCTION ESPECIALLY AUTOMOTIVE-TYPE EXHAUST GAS ANALYZING SENSOR

The present invention relates to the construction of an electrochemical sensor, and more particularly to a sensor suitable for use in an automotive-type internal combustion engine to provide an electrical output signal representative of the oxygen content of the exhaust gas from the engine.

BACKGROUND AND PRIOR ART

Various types of sensors are known, which operate on the basis of providing an output voltage when the composition of the exhaust gases changes from oxidizing to reducing state. One such sensor is described in German Disclosure Document DE-OS No. 27 29 475 to which U.S. Pat. No. 4,155,827 Maurer et al assigned to the assignee of this application, corresponds.

This type of sensor uses a solid electrolyte tube which is closed at one end. A heater element is located in the hollow space within the tube. Manufacture of a closed tube, with a heater element is comparatively difficult and hence expensive. It has also been proposed to use the plate-like solid electrolyte body made of oxygen ion conductive material, in which both electrodes are exposed to the gas to be tested. Such a potentiometric sensor has electrodes having different catalytic action with respect to catalyzing of the gas equilibrium at the surface of the solid electrolyte. Sensors of this type, provide, however, only low output voltage signals, less so than a sensor which uses a reference gas, such as air, separated from the test gas. In automotive applications, the small voltage differences sometimes can be masked by noise or disturbance signals arising within the vehicle, or due to passage of the vehicle close to external disturbing electromagnetic fields, such as high tension transmission lines, railroad catenary systems and the like.

THE INVENTION

It is an object to provide an electrochemical sensor construction which can be easily made and incorporated in a housing suitable for association with an automotive vehicle and in which exhaust gases and reference gases can be separated from each other so that the advantages of a potentiometric sensor with reference gas can be realized, without, however, requiring a structure such as a closed solid electrolyte tube.

Briefly, in accordance with the present invention, the sensor comprises a plate-like element made of oxygen ion conductive solid electrolyte material which has a test gas end portion carrying an electrode, and extending from a sensor housing into a space washed, or surrounded by test gas. The sensor housing then includes a sealing element which seals that portion from the remaining longitudinal extent of the solid electrolyte plate, the remaining extent of the solid electrolyte plate being exposed to a reference gas, typically oxygen in ambient air, which carries another electrode. Preferably, the electrodes are applied to a single side of the solid electrolyte plate, the other side thereof carrying a heater element which, preferably, is applied as a thin film deposited layer on the sensor plate.

The sensor construction has the advantage of ease of manufacture, since it is no longer required to apply a heater element at the inside of a closed tube; on the other hand, however, the advantage of high voltage output jumps upon transition of the exhaust gases from oxidizing to reducing state can be observed, which is an inherent advantageous characteristic of a potential metric sensor operating with a reference gas. The particular construction is suited for mass production technology so that it can be made inexpensively, and provides a substantially stronger output signal than a sensor, for example, as described in German Disclosure Document DE-OS No. 25 47 683 to which U.S. Pat. No. 4,157,282 Riddel, corresponds.

In addition to the there described sensor, a heater element can be applied to the sensor structure in accordance with any suitable well known mass production process, for example by printing, spraying or the like, or other thin film technology.

DRAWING

Figure 3:
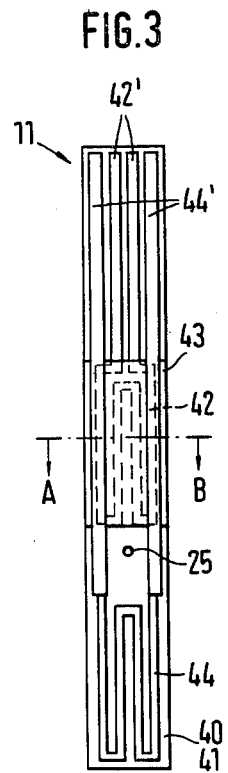
FIG. 3 is a plan view of the element of FIG. 1, rotated 180° with respect to the illustration of FIG. 2.
Figure 4:
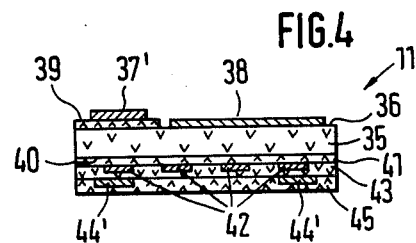

and FIG. 4 is a cross-sectional view through the sensor element along line A–B of FIG. 3, to a substantially enlarged scale.

The sensor 10 is used to determine oxygen content in gases, typically in combustion gases, and especially in the combustion exhaust gases from internal combustion engines. The sensor 10, essentially, has a plate-like sensing element 11, retained in a housing 12 which, preferably, is made of metal. The housing 12 is hollow and retains within the hollow interior 13 two ceramic holding elements 14, 15, a seal 16, and a protective sleeve or cap 17 surrounding the sensing end portion of the sensor 11. The cap 17 is formed with a gas inlet opening 18.

Figure 1:
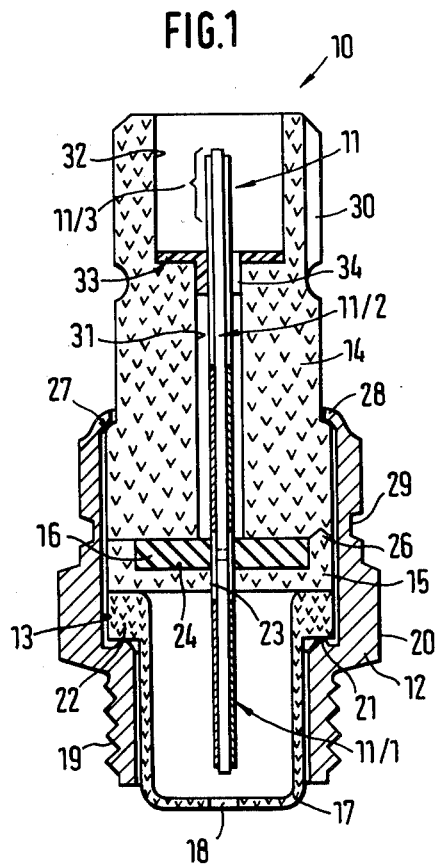
FIG. 1 is a schematic cross-sectional view through a sensor construction in a housing, omitting portions not necessary for an understanding of the present invention.

The housing 12 of the sensor has an outer thread 19 and a wrench-engagement surface 20, similar, for example, to the outer thread and wrench socket of an automotive-type spark plug. A shoulder 21 is formed in the interior of the housing which engages a flange 22 of the protective cap 17. The cap 17 is made of ceramic, but may be made of any other heat resistant material, for example, stainless steel or the like. Any suitable manner of securing the cap 17 in the housing can be used. More than one inlet opening 18 for the test gases may be provided, and the cap 17 may be made in accordance with various constructions, including, for example, gas directing vanes at the inside or outside thereof, or suitably shaped inlet openings. The lower side of the flange 28 of the cap 17 is engaged by the shoulder 21; the upper surface of the flange 22 is engaged by the ceramic holding portion 15 which has a central opening 23 and a pocket 24, facing the connecting portion, that is, in FIG. 1 the upper portion of the sensor 10. The pocket 24 receives the seal 16 for the sensor plate 11. Suitable sealing materials are ceramic cement, ceramic putty, glass, ceramic glass, or similar materials. The seal 16 additionally insures longitudinal retention of the sensor, and to hold the sensor securely and irremovably in position, the sensor is formed with a cross bore or opening 25 through which the sealing material can extend upon being compressed or flowing in the pocket 16. The sealing material thus will separate the sensor 11 into two sensing portions—a test gas sensing portion 11/1 and a reference gas or connecting portion 11/2.

The holder 14 made of ceramic, engages with its lower side to holder 15 and the seal 16. A protection 26 fitting within a matching recess formed on the engaging holders positions the ceramic elements 14, 15 with respect to each other. A shoulder 27 is formed on the outside of the ceramic element 14, engaged by an inwardly rolled edge 28 of the housing 12, and which retains the elements of the sensor in relatively fixed position after assembly. If necessary, and if an additional resilient connection is desired, a sealing ring, for example, of elastic material can be interposed between the outer shoulder 27 and the rolled-over edge 28 of the housing. The entire assembly can be held securely in compression by heat shrinking the housing 12. All the elements with which the housing 12 comes in contact are either metal or of ceramic material so that heat shrinking can be readily effected. The housing has a ring groove 29 at its outer edge to permit, after assembly, heating of the housing components by an induction coil, compression of the housing 12 while being heated and subsequent cooling of the housing while retaining the longitudinal compression force.

The outside of the ceramic holding portion 14 has a locating groove 30 formed therein to insure oriented attachment of an electric terminal plug to the sensor. The plug—which is external to the sensor—is not shown and may have any suitable shape.

A central opening 31 is formed in the ceramic holding portion 14, coaxial with the opening 23 and the holder 15. The central opening 31 extends along the remote portion 11/2 of the sensor and terminates in an enlarged opening 32. The sensor connecting portion 11/3 extends into the enlarged opening 32. A guide bushing 33 locates the sensor 11 in position within the opening 31 and the enlargement 32. The guide bushing 33, preferably, is made of plastic and is formed with a central opening 34 communicating with the opening 31 to permit ambient air to pass therethrough, and to provide reference oxygen to the space within the bore 31, and thus to provide reference oxygen to the sensor 11.

The construction described is a preferred form of a holder of a plate-like sensing element; various change and modifications of the construction may be made, of course, to accomodate particular holder or housing arrangements for example.

Figure 2:
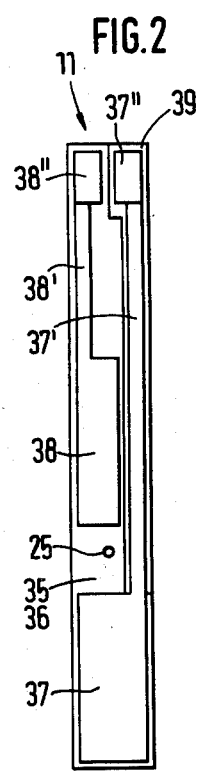
FIG. 2 is a plan view of the sensor element of FIG. 1, rotated 90° with respect to the illustration of FIG. 1.

The elongated plate-like sensor 11 consists of oxygen ion conductive solid electrolyte material, such as stabilized zirconium dioxide and forms an elongated plate-like carrier 35 (see FIG. 2) having two major surfaces 36 (FIG. 2) and 40 (FIG. 3). The major surface 36 has a porous sensing electrode 37, made of platinum applied thereto, and a reference electrode 38, likewise made of porous platinum. The electrodes 37, 38 can be applied in accordance with any well known method, for example, by printing. The shape of the electrodes is best seen in FIG. 2. The two electrodes 37, 38 are connected by means of conductive tracks 37', 38' to the connecting portion 11/3 of the sensor, to form electrical connecting terminals 37'', 38''. The connections 37', 38' are applied, for example, concurrently with application of the electrode 37, 38 by any suitable and well known method, such as printing, vapor deposition or the like on the carrier 35. The conductive track 37' and the electrical terminal 37'' of the sensing electrode 37 are separated from the solid electrolyte body by an electrically insulating layer 39, for example, of aluminum oxide, or any other suitable thin insulating layer.

The sensing electrode 37 is located at the sensing end portion 11/1 of the sensor 11. The reference electrode 38 is located at the reference portion 11/2 of the sensor 11, separated therefrom by a space in which the seal 16 can engage, and through which the opening 25 passes. The reference portion 11/2 is exposed to oxygen, for example the oxygen in ambient air, passing through opening 34 of the terminal bushing and present within the space 31 of holder element 14. The sensing electrode 37 preferably is covered with a porous protective layer—not shown—which increases the lifetime of the structure, specifically of the sensing electrode 37, and which can be made of highly porous magnesium spinel. Such porous protective structures are well known. A transverse opening 25 located in the carrier 35 is positioned between the two electrodes 37, 38 and insures longitudinal positioning of the sensor carrier 35 within the housing structure. Rather than making the solid electrolyte body of a single oxygen ion conductive solid electrolyte carrier 35, the plate or carrier 35 can be an inert, or electrically inactive carrier, for example an elongated plate made of aluminum oxide on which a thin layer of oxygen ion conductive solid electrolyte material is applied which then need to cover only the portion of the sensing region, that is, the sensing portion 11/1 and the reference portion 11/2 of the sensor 11.

In accordance with yet another embodiment, the carrier 35 may be made of a metal which is coated with an electrically insulated layer, on which, again, a thin layer of solid electrolyte material is applied over which the electrodes are then applied as described.

The sensor, as described, operates in accordance with the potentiometric principle, that is, it provides an electrochemical cell which has a certain output voltage level if the stoichiometric ratio of oxygen to fuel in the test gas is greater than 1 but a substantially higher output voltage level if the stoichiometric ratio of oxygen to fuel in the test gas is lower than 1. The evaluation circuitry to evaluate the presence or absence of oxygen in the test gas, then, can be electronically simple. The sensing structure may be used, however, also to operate as a polarographic sensor, in which a voltage is applied between the two electrodes 37, 38, current flow there between evaluated. This current flow, which will be the diffusion limiting current, then can be evaluated and represent a measure of oxygen concentration of the test gas. If the sensor structure is to operate in the polarographic mode, a suitable diffusion barrier for oxygen molecules should be applied to the sensing electrode. Such a diffusion barrier may be a thin layer of predetermined porosity to provide a predetermined gas diffusion resistance or barrier, as explained, for example, in German Disclosure Document DE-OS No. 27 11 880, U.S. Application Ser. No. 6,093 filed Jan. 24, 1979, Dietz, assigned to the assignee of this application. The material, may, again, be magnesium spinel, applied to have the relative thickness and porosity to permit this layer to operate as a diffusion barrier, rather than merely as a protective layer. A protective layer of substantially higher porosity can be applied thereover. The sensing electrode and the reference electrode 38, 39 will have constant voltage applied thereto.

An electrical insulating layer 41 is applied to the second major surface 40 of the carrier 35—see FIG. 3—unless the carrier 35 itself is of insulating material. A suitable insulating layer may, for example, be aluminum oxide. The electrically insulating layer 41, in the reference portion 11/2 of the sensor additionally has a heating element 42 applied thereto, in accordance with any well known method, such as by printing, vapor deposition or the like, and which is located essentially beneath the reference electrode 38, and connected by conductive tracks 42 with the connecting portion 11/3 of the sensor plate. The heater element 42, and the conductive tracks 42' may, for example, consist of platinum. An electrically insulating layer 43 is applied over the heater tracks and the heater, which, again, may consist of aluminum oxide and which separates the heater tracks 44' leading to a heater element 44. The heater element 44 is positioned in alignment with the sensing portion 11/1 of the sensor, and the conductive tracks 44' are separated from the conductive tracks 42' supplying the heater 42. The heater element 44 preferably has a protective layer 45 applied thereover in order to extend the lifetime of the heater element 44, the protective layer, for example, consisting of aluminum oxide. Use of two separate elements 42, 44 separate, independent control of heater power of the heater elements which are applied to the plate 35 to heat the respective test gas or reference gas electrodes. In some structures, where this is not needed, a single heater 42, for example, may suffice since the test gas electrode is heated by the high temperature of the exhaust gases themselves. Or, a single heater can be used extending longitudinally across both electrodes. Any suitable arrangement, indepence on the design requirements of the sensor can be used.

A thermocouple or other thermal sensing element can be located on the sensor 11 in either one of the regions 11/1, or 11/2 in order to permit control of heater power supplied to the respective heater elements 42, 44.

The structure, as explained, is the preferred arrangement, in which the reference electrode 38 and the sensing electrode 37 are located on a single side 36 of the sensor carrier. It is also possible, however, to apply the sensing electrode 37 on one side, for example, 36, and the reference electrodes 38 on the other side 40 of the sensing element. The respective heater elements can then be applied to the carrier plate or a suitable insulating layer to electrically galvanically separate the heater and the conductive tracks thereto from the remainder of the sensing structure.

Various changes and modifications may be made within the scope of the inventive concept.

I claim:

1. Electrochemical sensor construction, particularly for incorporation in the exhaust system of an automotive-type internal combustion engine comprising
  a tubular housing (12);
  an elongated plate (11) of an oxygen ion conductive solid electrolyte material having one end portion exposed to the exhaust gases and forming a sensing portion (11/1) and another end portion adapted for connection to an external circuit, and forming a connecting portion (11/3);
  electrodes (37, 38) secured on a surface of the plate;
  and heating means on the plate to maintain at least selected regions of the plate at an elevated temperature
  comprising, in accordance with the invention
  a seal (16) separating, in gas-tight manner, said sensing end portion (11/1) of the plate from the remainder of the plate and securing the elongated plate into the housing at an intermediate portion;
  the portion of the sensor remote from said sensing end portion at the other side of the seal, and inwardly of the connecting portion (11/3) forming a reference portion (11/2) and being exposed to a reference substance;
  and wherein one of the electrodes (37) is positioned on the measuring end portion and the other electrode (38) is positioned on the reference portion;
  and wherein, further, said heating means comprises a flat heating layer applied to a surface of the plate opposite at least the electrode (38) on the reference portion (11/2).

2. Sensor according to claim 1, wherein the reference substance comprises oxygen of ambient air, and said sensor housing includes access openings (31, 34) establishing communication of ambient air with the reference portion (11/2).

3. Sensor according to claim 2, wherein the heating means comprises a thin film layer on a flat surface of the elongated plate (11).

4. Sensor according to claim 1, wherein both the first and the second electrodes (37, 38) are located on the same major surface (36) of the elongated plate.

5. Sensor according to claim 4, wherein the heater element is a thin film heater element located at the side of the plate opposite that at which the electrodes are applied.

6. Sensor according to claim 5, wherein the heater element and at least one electrode are in at least approximately matching registration.

7. Sensor according to claim 5, wherein two heater elements are provided, one, each, in approximately matching registration with one of the electrodes.

8. Sensor according to claim 1, wherein both the electrodes are of essentially the same material and the sensor operates as a potentiometric cell.

* * * * *